United States Patent [19]
Kim et al.

[11] Patent Number: 5,662,917
[45] Date of Patent: Sep. 2, 1997

[54] RELEASE-CONTROLLED IMPLANTABLE SOMATOTROPIN COMPOSITION

[75] Inventors: Nam Joong Kim; Heung Soo Cho; Maeng Seok Song; Yun Jeong Choi; Byung Geon Rhee, all of Daejeon, Rep. of Korea

[73] Assignee: Lucky Limited, Seoul, Rep. of Korea

[21] Appl. No.: 601,275

[22] Filed: Mar. 22, 1996

Related U.S. Application Data

[63] Continuation of Ser. No. 171,533, Dec. 22, 1993, abandoned.

[30] Foreign Application Priority Data

Dec. 28, 1992 [KR] Rep. of Korea ............... 92-25904

[51] Int. Cl.$^6$ ............... A61K 9/22; A61K 38/27
[52] U.S. Cl. ............ 424/422; 424/423; 424/426; 424/450; 424/464; 424/468; 424/469; 424/489; 424/499; 424/501; 424/502; 424/484; 424/486; 514/2; 514/21
[58] Field of Search ............ 424/450, 422, 424/423, 426, 464, 468, 469, 489, 499, 501, 502, 484, 486; 514/2, 21

[56] References Cited

U.S. PATENT DOCUMENTS

| | | | |
|---|---|---|---|
| 4,765,980 | 8/1988 | DePrince et al. | 424/8 |
| 4,837,381 | 6/1989 | Steber | 424/502 |
| 5,110,595 | 5/1992 | Wang | 424/422 |
| 5,219,572 | 6/1993 | Sivaramakrishnan | 424/438 |
| 5,225,212 | 7/1993 | Martin | 424/450 |

FOREIGN PATENT DOCUMENTS

| | | |
|---|---|---|
| 246 540 A2 | 11/1987 | European Pat. Off. |
| 462 959 A1 | 12/1991 | European Pat. Off. |
| 90/11070 | 10/1990 | WIPO |
| 91/05548 | 5/1991 | WIPO |

*Primary Examiner*—Gollamudi S. Kishore
*Attorney, Agent, or Firm*—Anderson, Kill & Olick P.C.

[57] ABSTRACT

The present invention relates to a release-controlled implantable composition comprising somatotropin, a biocompatible wax and a water-soluble polymer. The present composition exhibits superior sustained effect with little side effects, which renders it suitable for long-term administration.

9 Claims, 4 Drawing Sheets

● : Example 7
▼ : Example 8
■ : Example 9
○ : Comparative Example 2
▽ : Control

RELEASE-CONTROLLED IMPLANTABLE SOMATOTROPIN COMPOSITION

This is a continuation of application Ser. No. 08/171,533 filed Dec. 22, 1993 now abandoned.

FIELD OF THE INVENTION

The present invention relates to a release-controlled implantable somatotropin composition; and, in particular, to a release-controlled implantable somatotropin composition which provides a sustained release of biologically active somatotropin when administered parenterally into animals and human beings.

DESCRIPTION OF THE PRIOR ART

Most of the biologically active somatotropins have a relatively short in vivo half-life. In order to provide sufficiently high biological effects and maintain prolonged biological activities of somatotropin, therefore, the formulation need be administered excessively and/or frequently, which may cause serious side effects to the subject administered therewith. Accordingly, in case of administering somatotropin in vivo, it requires an innocuous scheme of prolonging its effect. Consequently, various attempts have been made to develop a somatotropin composition having a prolonged release characteristic which makes it possible to reduce the frequency/dosage of its administration.

Most release-controlled somatotropin compositions available hitherto are of an injectable formulation. For example, Korean Patent Publication No. 89-2631 and Korean Patent Laid-open Publication No. 87-1825 disclose a composition comprising a transition metal/somatotropin complex in an oil-suspended vehicle made of a vegetable or mineral oil mixed with excipients and adjuvants.

European Patent Publication Nos. 1986/193,917 and 1989/314,421 describe a composition comprising a biologically active macromolecule of growth hormone dispersed in water or in an oil with a carbohydrate polymer such as dextran.

European Patent Publication No. 1987/211,691 also provides a composition comprising somatotropin dispersed in a vegetable oil with several waxes. Korean Patent Publication No. 92-5688 and Korea Patent Laid-open Publication No. 92-11513 offer a composition comprising somatotropin dispersed in tocopherol acetate.

The compositions described above, however, have such defects as burst effect; and, consequently, alternative methods of administering the biologically active somatotropin in vivo by way of using, e.g., an implantable formula have been sought.

For instance Korean Patent Publication No. 90-6886 teaches a method for manufacturing an implantable pellet which comprises coating a somatotropin grain with a partial barrier coating of polymers, such as shellac, beeswax and cellulose to control the release of somatotropin. Likewise, Korean Patent Publication No. 93-8952 illustrates a method for manufacturing an implantable formulation in a pellet form which comprises the steps of mixing somatotropin, sucrose and ethyl cellulose, formulating the mixture into pellets and coating the pellets with a microporous or non-porous polyethylene.

European Patent Publication No. 1991/462,959 also discloses a method of manufacturing an implantable formulation which comprises coating the pellets of metal/somatotropin complex with polyvinyl acetate having various molecular weights and concentrations. Likewise, U.S. Pat. No. 4,765,980 teaches an implantable formulation comprising an ion/somatotropin complex in a silicon tube. Korean Patent Laid-open Publication No. 93-12035 also shows a method of manufacturing an implantable tablet which comprises the steps of granulating a mixture of somatotropin and a water-soluble polymer and coating the granules with hydroxymethyl cellulose.

PCT International Publication No. WO90/11070 provides an implantable somatotropin pellet prepared by using a solvent and a water-insoluble polymer. PCT International Publication No. WO91/05548 discloses an implantable composition comprising somatotropin dispersed in a mixture of a wax and a surfactant.

However, the above implantable compositions often fail to maintain a sustained-release of somatotropin for a desired period, and/or need complicated manufacturing processes such as incorporation of complex metal ion, coating of formulation, etc. Moreover, upon administration into an organism, they tend to be encapsulated by fibrous tissues due to their incompatibility with the tissues of the organism, which may bring about serious consequences.

On the other hand, European Patent Publication No. 1987/246,540 discloses a method for preparing an implantable formulation which comprises admixing somatotropin with a fatty acid homogeneously and formulating it into a desired form. Although, said method may be applied easily to drugs having a lower concentration requirement, e.g., insulin, it is rather difficult to apply the technique to those drugs requiring a higher effective concentration, e.g., somatotropin, because of the poor release rate of the formulation.

SUMMARY OF THE INVENTION

Accordingly, it is a primary object of the present invention to provide an implantable somatotropin composition capable of releasing the biologically active somatotropin in a time-controlled manner without any residual problem when administered in vivo and which can be prepared via a simple process.

In accordance with the present invention, there is provided a novel implantable somatotropin composition consisting of a homogeneous mixture of a somatotropin, polyethylene glycol and a biocompatible wax.

BRIEF DESCRIPTION OF THE DRAWINGS

The above and other objects and features of the present invention will become apparent from the following description of preferred embodiment taken in conjunction with the accompanying drawings, in which.

DETAILED DESCRIPTION OF THE PREFERRED EMBODIMENTS

Figure 1:
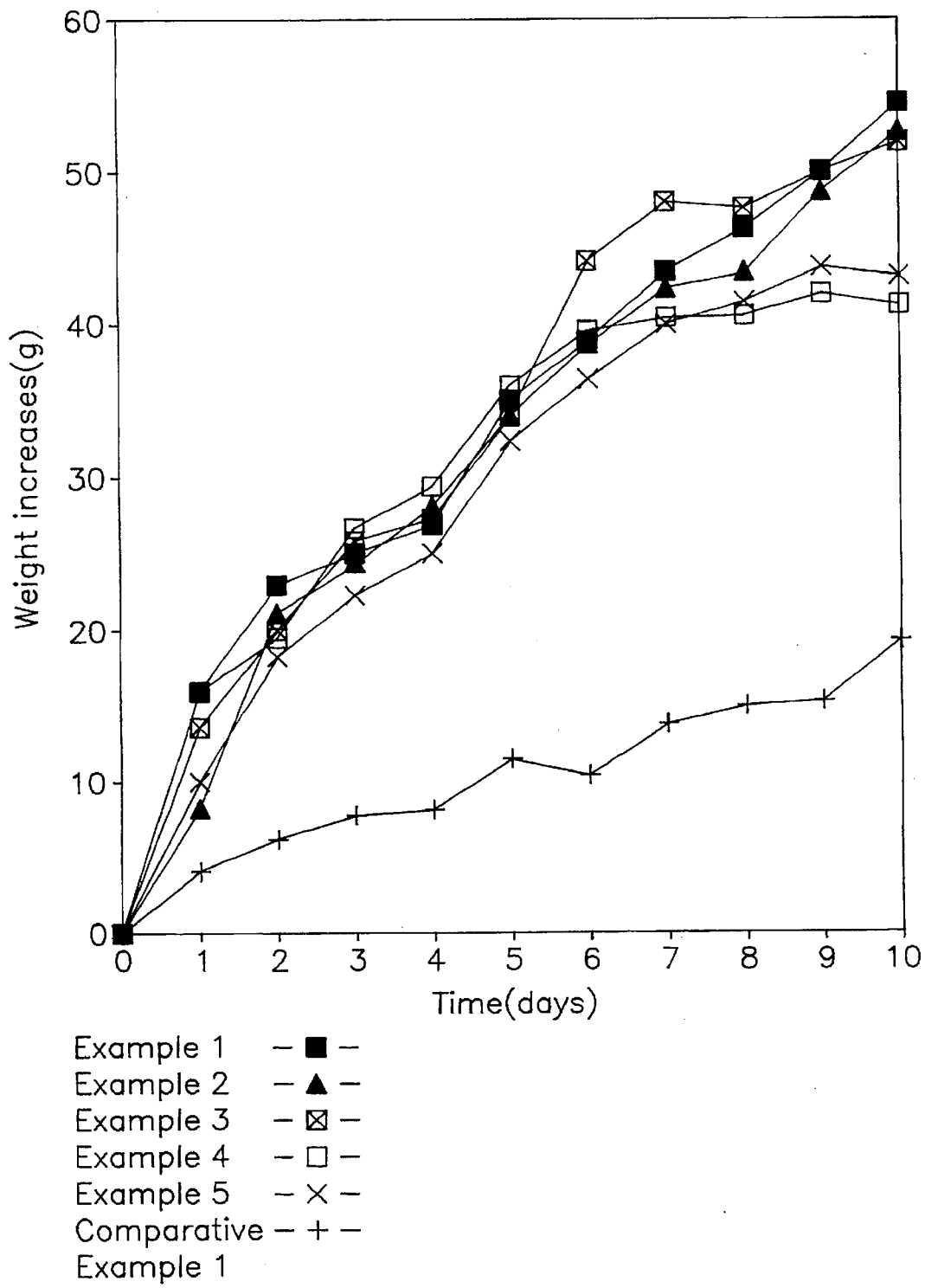
FIG. 1 shows the effects of exemplary compositions comprising porcine somatotropin, prepared in accordance with the present invention, on the weight gain when they are administered to rats.
Figure 2:
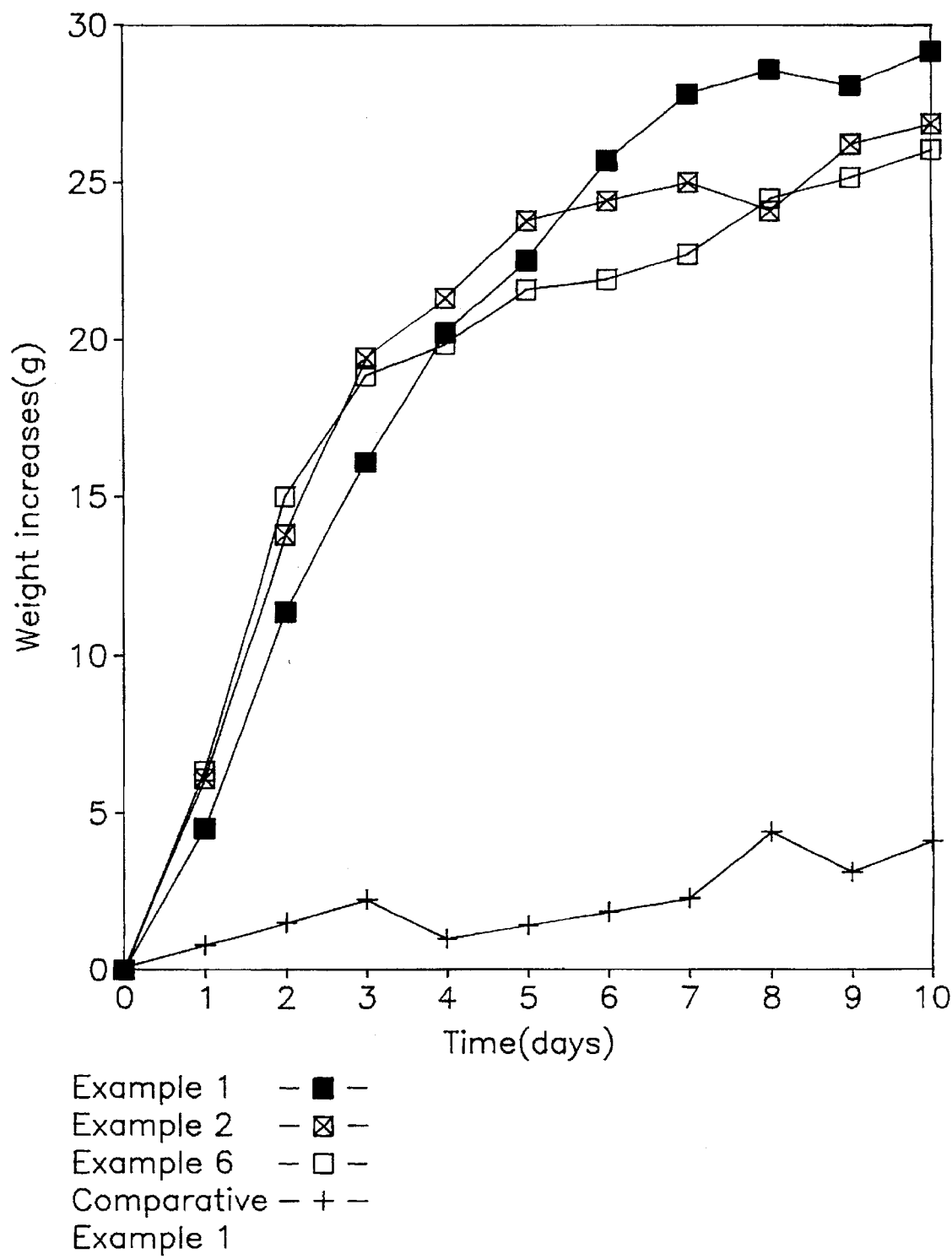
FIGS. 2 and 3 show the effects of the exemplary compositions comprising porcine somatotropin on the weight gain when they are administered to hypophysectomized rats.
Figure 3:
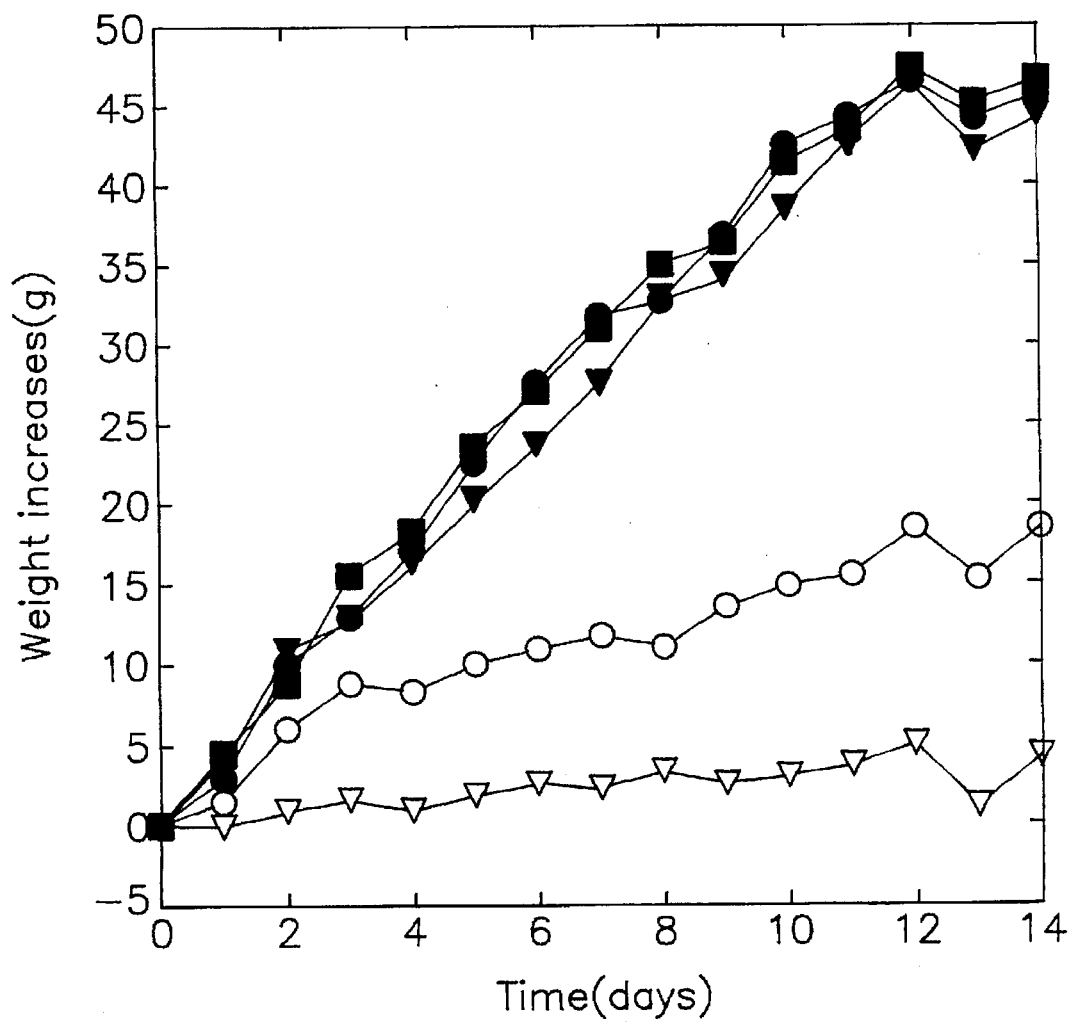
Figure 4:
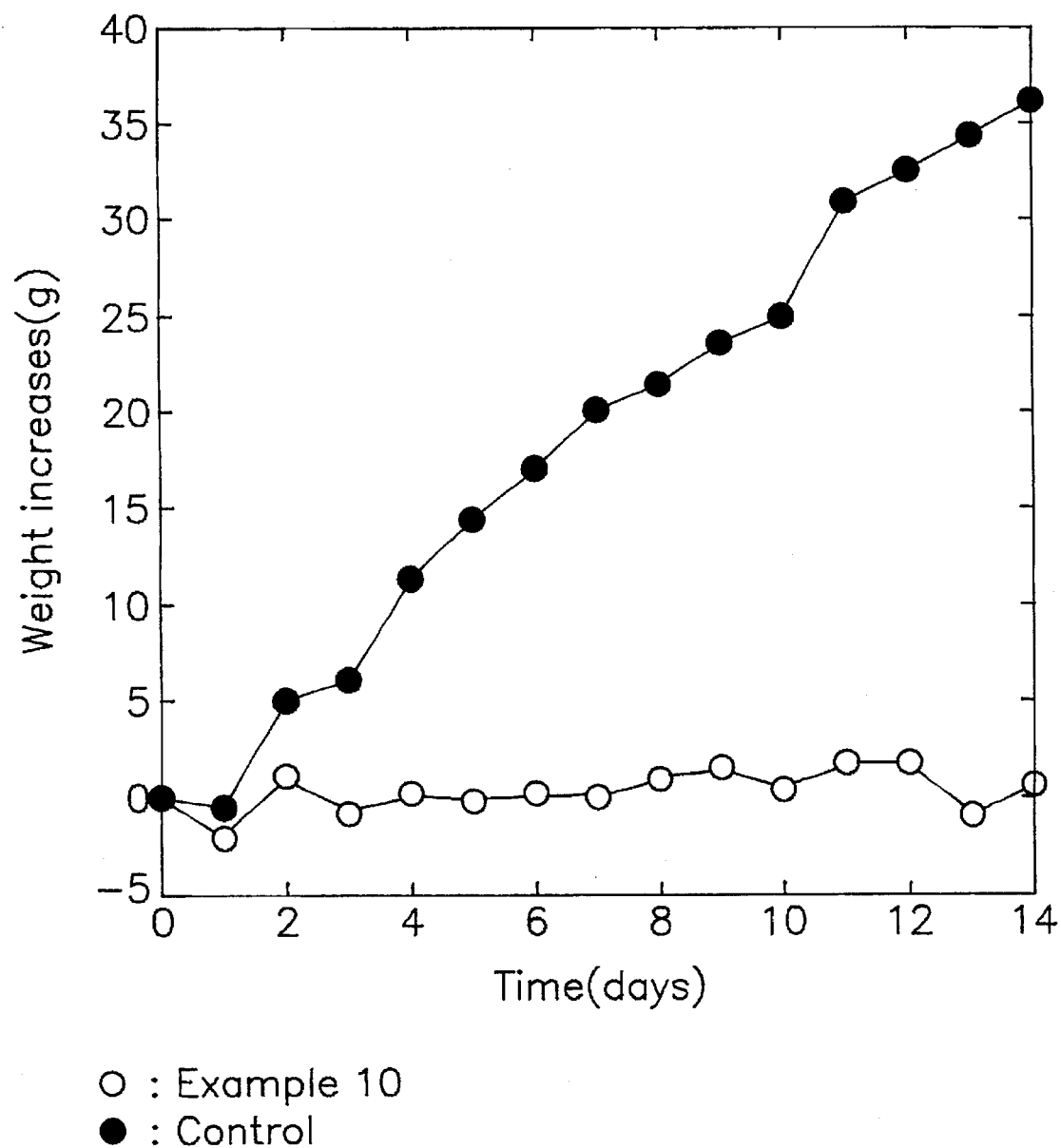
FIG. 4 shows the effects of the exemplary compositions comprising bovine somatotropin on the weight gain when they are administered to hypophysectomized rats.

In accordance with the present invention, polyethylene glycol, a biocompatible wax and lyophilized somatotropin powder are mixed homogeneously to obtain the composition of the present invention and the resulting composition can be formulated into various matrix forms as desired.

Polyethylene glycols which may be used in the present invention are those having a molecular weight ranging from 1,000 to 40,000 daltons, preferably from 1,540 to 35,000 daltons. They may be employed alone or in combination with each other having different molecular weights within the above range. The amount of polyethylene glycol used in the composition may range from 30 to 50% by weight based on the total weight of the composition.

The biocompatible wax which may be used in the composition of the present invention includes a paraffin wax and white beeswax, etc.; and can be used in an amount from 30 to 50% by weight based on the total weight of the composition.

The biologically active somatotropin for use in the present composition is any of those lyophilized, which may be used alone or mixed with a lecithin, e.g., L-alpha-phosphatidyl choline; and may include animal growth hormones, preferably bovine somatotropin or porcine somatotropin. They can be extracted from the animals or produced by using a recombinant DNA technology from the culture of microorganisms.

The composition of the present invention may be formulated into various matrix forms suitable for administration, for example, a tablet or a pellet.

The size and level of active ingredient of the formulation may vary depending on the desired amount of biologically active somatotropin but within a range not to incur rejection or adverse effect in the subject organism. In case of a tablet, it may have a size ranging from 3 to 15 mm in diameter and from 1 to 10mm in thickness.

The following Examples are given for the purpose of illustration only and are not intended to limit the scope of the invention.

EXAMPLE 1

5 g of lyophilized porcine somatotropin powder was mixed with 10 g of polyethylene glycol having a molecular weight of 35,000 and 10 g of paraffin wax, and then the mixture was mixed homogeneously by using a ball mill.

250 mg of the homogeneously mixed composition obtained above was formed into a tablet having the size of 7 mm in diameter and 6.2 mm in thickness by using a tabletting machine(KORSCH, MASCHINENFABRIK, Germany).

EXAMPLE 2

The same procedures as described in Example 1 were repeated by using a polyethylene glycol having a molecular weight of 20,000 instead of 35,000.

EXAMPLE 3

The same procedures as described in Example 1 were repeated by using a polyethylene glycol having a molecular weight of 12,000 instead of 35,000.

EXAMPLE 4

The same procedures as described in Example 1 were repeated by using a polyethylene glycol having a molecular weight of 8,000 instead of 35,000.

EXAMPLE 5

The same procedures as described in Example 1 were repeated by using a polyethylene glycol having a molecular weight of 1,540 instead of 35,000.

EXAMPLE 6

The same procedures as described in Example 1 were repeated except that a lyophilized liposomal porcine somatotropin(the porcine somatotropin mixed with L-alpha-phosphatidyl choline, which was prepared according to a method disclosed in Korean Patent Application No. 90-23104) was used in place of the lyophilized porcine somatotropin and that 266.5 mg tablet was prepared.

COMPARATIVE EXAMBLE 1

The same procedures as described in Example 1 were repeated without porcine somatotropin.

The physical properties of the tablet such as hardness and moisture content were determined. The hardness of the tablet was measured by using a hardness tester(ERWEKA, TBH-28), and the moisture content of the tablet was analyzed by using a moisture analyzer(Sartorius Moisture Analyser)(see Table 1).

The physical properties of the tablets prepared in Examples 1 to 6 and Comparative Example 1 are shown in Table 1.

TABLE 1

| | Physical properties of the tablets | | | | | | |
|---|---|---|---|---|---|---|---|
| | Example 1 | Example 2 | Example 3 | Example 4 | Example 5 | Example 6 | Comparative Example 1 |
| hardness (N) | 88.0 ± 4.30 | 83.8 ± 2.80 | 83.2 ± 2.62 | 91.5 ± 1.59 | 76.5 ± 2.43 | 74.7 ± 3.10 | 46.4 ± 1.15 |
| moisture content (%) | 1.06 | 0.87 | 1.39 | 1.42 | 1.13 | 1.12 | 0.49 |

The release rates of the tablets prepared in Examples were tested as described hereinbelow.

In Vitro Dissolution Test

To a solution vessel of a dissolution tester(CALEVA Model 7ST) were added 400 ml of 10 mM phosphate buffered saline, pH 7.3 and a tablet prepared in each of Examples 1 to 5; and, under the condition of 37° C. and 100 rpm, the absorbance of the solution at 280 nm was measured by using a spectrophotometer at an interval of 2 hours for 24 hours.

The tyrosine, phenylalanine and tryptophan residues of somatotropin absorb ultraviolet light having the wave lengths of 275 nm and 280 nm. The combined level of the above amino acids in somatotropin is almost constant, and, therefore, the concentration of somatotropin is proportional to the absorbance at 280 nm. In case of pure somatotropin, absorbance at 280 nm is measured as 1.0 when the concentration of somatotropin is 1 mg/ml and the path length of ultraviolet light is 1 cm.

Accordingly, the amount of released somatotropin can be calculated easily from the following equation:

Released amount of somatotropin(mg)=Absorbance at 280 nm(O.D.)×volume of the solution used in the dissolution test(ml)

The linear equation for the amount of the somatotropin released from each composition(prepared in Examples 1 to 5) against elapsed time, i.e., y=ax+b(wherein y is the amount of the somatotropin released, x is the elapsed time, and coefficients a and b represent the slope and the intercept, respectively) was obtained with the coefficients as shown in Table 2. The correlation coefficient, r, was obtained by the least square method and represents the linearity of the test results.

TABLE 2

Coefficients for the linear equation representing the relationship between released amount and elapsed time (y = ax + b)

| coefficients | Example 1 | Example 2 | Example 3 | Example 4 | Example 5 |
|---|---|---|---|---|---|
| slope (a) | 0.0380 | 0.0089 | 0.0084 | 0.0051 | 0.0087 |
| intercept (b) | 0.0042 | 0.0181 | 0.0131 | 0.0025 | 0.0063 |
| correlation coefficient (r) | 0.9905 | 0.9922 | 0.9920 | 0.9817 | 0.9912 |

In Vivo Effectiveness Test (1) Effect on increase of body weight of normal rats

The effects of the somatotropin compositions of the present invention on body weight were determined by in vivo test using the tablets prepared in Examples 1 to 5 and Comparative Example 1. Thirty female SD rats(Toxicology Research Center, Korea Research Institute of Chemical Technology, Daejeon, Korea) weighing 200–250 g were incised in subcutis of left-back, and, then, the tablets obtained in Examples 1 to 5 were implanted thereto for each group of 5 rats, respectively, and the incised skin was sutured. A sixth group of five rats implanted with the tablets obtained in Comparative Example 1 was used as a control group. The rats were weighed everyday at the same time for 10 days after the implantation and their weights were compared with those obtained shortly before the implantation to determine their weight increases, which are shown in Table 3.

the operation, they were weighed everyday at the same time for 1 week for selecting sixteen rats whose weight remained least changed. The tablets prepared in the above were implanted into the incised subcutis of left-back of three groups of four rats, respectively; and the incised skin was sutured. 50 mg of the composition of Comparative Example 1 was made into a tablet having the same size as above; and each of four rats implanted with this tablet was used as a control group. The sixteen rats were weighed everyday at the same time for 10 days and the measured weights were compared with those measured 3 days before the implantation to determine their weight increases. The results are shown in Table 4, wherein the weight increases are given as mean value ± standard deviation.

TABLE 4

| | Weight increases of hypophysectomized rats (g) | | | |
|---|---|---|---|---|
| day | Composition of Example 1 | Composition of Example 2 | Composition of Example 6 | Comparative Example 1 |
| 1 | 4.68 ± 0.43 | 5.73 ± 0.88 | 5.83 ± 0.65 | 0.60 ± 1.08 |
| 2 | 11.60 ± 0.78 | 13.58 ± 1.24 | 14.88 ± 0.45 | 1.25 ± 0.76 |
| 3 | 16.23 ± 0.62 | 19.33 ± 1.70 | 19.00 ± 1.66 | 1.70 ± 0.56 |
| 4 | 20.23 ± 1.53 | 21.23 ± 2.29 | 20.08 ± 2.25 | 0.77 ± 0.82 |
| 5 | 22.68 ± 1.63 | 24.10 ± 2.13 | 21.68 ± 2.24 | 0.95 ± 0.88 |
| 6 | 25.38 ± 2.23 | 24.53 ± 3.02 | 22.15 ± 2.72 | 1.47 ± 1.50 |
| 7 | 27.88 ± 2.02 | 24.95 ± 2.59 | 22.85 ± 2.48 | 1.95 ± 1.02 |
| 8 | 28.68 ± 2.98 | 24.20 ± 2.83 | 24.47 ± 3.10 | 4.33 ± 1.39 |
| 9 | 28.45 ± 3.32 | 25.93 ± 2.57 | 24.87 ± 2.82 | 3.13 ± 1.70 |
| 10 | 29.15 ± 2.66 | 26.63 ± 3.13 | 25.90 ± 3.84 | 3.93 ± 1.73 |

EXAMPLE 7

50 mg(containing 10 mg of porcine somatotropin) of the composition of Example 1 was made into a tablet having the size of 4 mm in diameter and 3.6 mm in thickness in accordance with the procedures described in Example 1.

EXAMPLE 8

40 mg(containing 10 mg of porcine somatotropin) of the composition, which was prepared in accordance with the

TABLE 3

| | Weight increases in rats (g) | | | | | |
|---|---|---|---|---|---|---|
| day | Example 1 | Example 2 | Example 3 | Example 4 | Example 5 | Comparative Example 1 |
| 1 | 15.20 ± 1.77 | 8.32 ± 2.90 | 13.68 ± 0.98 | 15.16 ± 1.59 | 10.30 ± 1.60 | 4.63 ± 0.94 |
| 2 | 22.68 ± 2.08 | 20.72 ± 2.70 | 20.40 ± 1.66 | 20.10 ± 1.32 | 18.00 ± 1.46 | 6.38 ± 1.45 |
| 3 | 24.54 ± 2.60 | 24.20 ± 1.56 | 24.78 ± 2.19 | 25.26 ± 1.24 | 22.06 ± 1.84 | 7.65 ± 1.83 |
| 4 | 27.14 ± 3.36 | 28.48 ± 2.11 | 27.60 ± 3.12 | 29.20 ± 1.21 | 25.06 ± 2.06 | 8.05 ± 1.07 |
| 5 | 34.70 ± 3.28 | 33.66 ± 1.64 | 33.34 ± 2.92 | 34.92 ± 1.62 | 32.00 ± 1.50 | 11.55 ± 1.40 |
| 6 | 38.74 ± 4.24 | 38.98 ± 2.21 | 44.24 ± 3.55 | 39.02 ± 0.46 | 36.46 ± 1.56 | 10.23 ± 1.38 |
| 7 | 43.08 ± 4.36 | 42.20 ± 1.59 | 47.72 ± 4.29 | 40.68 ± 2.26 | 40.26 ± 2.55 | 13.20 ± 1.76 |
| 8 | 45.86 ± 4.74 | 43.72 ± 2.76 | 47.38 ± 6.17 | 41.20 ± 1.90 | 41.52 ± 2.34 | 14.98 ± 2.20 |
| 9 | 50.56 ± 4.17 | 49.64 ± 1.48 | 50.20 ± 5.24 | 42.20 ± 2.23 | 44.14 ± 2.58 | 15.05 ± 1.48 |
| 10 | 54.26 ± 4.51 | 52.68 ± 0.87 | 52.10 ± 4.37 | 42.00 ± 1.25 | 43.36 ± 4.35 | 19.04 ± 2.05 |

(2) Effect on increase of body weight of hypophysectomized rats

Each 50 mg of the compositions of Examples 1, 2, and 6 was made into a tablet having the size of 7 mm in diameter and 1.4 mm in thickness in accordance with the procedure described in Example 1. The effects of the compositions of the present invention on the weight gain of hypophysectomized rats were determined by in vivo test using the above tablets. Female SD rats weighing 80–120 g were undergone hypophysectomy by using the parapharyngeal method(H. B. Waynforth, Experimental and Surgical Technique in the Rat, pp 143–150, Academic Press (1980)). From two weeks after procedures described in Example 1, except that 7.5 g of polyethylene glycol (MW=35,000) and 7.5 g of paraffin wax were used, was made into a tablet by employing the procedures described in Example 7.

EXAMPLE 9

30 mg(containing 10 mg of porcine somatotropin) of the composition, which was prepared in accordance with the procedures described in Example 1, except that 5 g of polyethylene glycol (MW=35,000) and 5 g of paraffin wax were used, was made into a tablet by employing the procedures described in Example 7.

COMPARATIVE EXAMPLE 2

According to Example 3 contained in European Patent Publication No. 1987/246,540, 32.5 mg of palmitic acid, 7.5 mg of cholesterol and 10 mg of porcine somatotropin were mixed homogeneously by using a ball mill and then 50 mg of the composition was made into a tablet having the size of 4 mm in diameter and 3.6 mm in thickness.

In vivo test with hypophysectomized rats was carried out in accordance with the procedures as described previously by using the tablets prepared in Examples 7 to 9 and Comparative Example 2.

The results are shown in Table 5 below. In Table 5, the weight increases are given as mean ± standard deviation and non-treated hypophysectomized rats were used as a control group.

EXAMPLE 11

Increased weight and feed efficiency of hogs implanted with a porcine somatotropin composition of the present invention were measured for 4 weeks after the implantation. The test was carried out using 12 male hogs weighing about 75 kg.

Each tablet weighing 500 mg(containing 100 mg of porcine somatotropin) prepare in Example 1 was implanted into the subcutis of each of 6 hogs every 2 weeks. The other 6 hogs were used as a control group without any treatment. The weight of hogs was measured before the implantation, and 2 weeks and 4 weeks after the implantation. The average daily gain(ADG), the amount of feed intake and the feed efficiency (the amount of feed intake/the amount of body weight increases) were calculated and are shown in Table 7 together with the increased weight.

TABLE 5

| | Weight increases in hypophysectomized rats (g) | | | | |
|---|---|---|---|---|---|
| day | Example 7 | Example 8 | Example 9 | Comparative Example 2 | Control |
| 1 | 2.7 ± 1.22 | 4.6 ± 1.37 | 4.2 ± 1.10 | 1.3 ± 0.56 | −0.1 ± 0.43 |
| 2 | 9.4 ± 1.99 | 10.1 ± 1.33 | 8.9 ± 1.36 | 5.9 ± 0.58 | 0.6 ± 0.60 |
| 3 | 12.9 ± 1.56 | 12.8 ± 0.86 | 15.2 ± 0.89 | 8.9 ± 0.31 | 1.3 ± 0.87 |
| 4 | 17.6 ± 2.20 | 16.7 ± 1.14 | 18.4 ± 1.25 | 8.6 ± 0.46 | 1.1 ± 0.85 |
| 5 | 22.8 ± 2.64 | 20.7 ± 1.73 | 23.8 ± 1.33 | 9.9 ± 0.32 | 1.6 ± 0.97 |
| 6 | 27.4 ± 2.51 | 23.9 ± 1.44 | 26.9 ± 2.19 | 11.2 ± 0.36 | 1.9 ± 1.49 |
| 7 | 31.2 ± 2.49 | 27.9 ± 2.48 | 30.8 ± 2.68 | 11.8 ± 0.83 | 2.3 ± 1.67 |
| 8 | 33.0 ± 1.84 | 33.3 ± 2.85 | 34.9 ± 2.62 | 11.5 ± 0.26 | 3.1 ± 1.44 |
| 9 | 37.7 ± 2.28 | 35.9 ± 2.79 | 37.5 ± 2.45 | 13.7 ± 0.58 | 2.5 ± 1.44 |
| 10 | 42.4 ± 3.60 | 38.9 ± 3.16 | 41.3 ± 2.62 | 14.8 ± 1.45 | 2.8 ± 1.55 |
| 11 | 44.3 ± 3.91 | 43.1 ± 3.43 | 44.0 ± 2.71 | 15.3 ± 0.92 | 3.6 ± 1.47 |
| 12 | 46.6 ± 4.49 | 46.5 ± 3.86 | 47.2 ± 2.85 | 18.2 ± 0.12 | 5.2 ± 1.00 |
| 13 | 44.2 ± 3.72 | 42.6 ± 3.47 | 45.1 ± 3.22 | 15.4 ± 0.61 | 1.6 ± 0.70 |
| 14 | 45.8 ± 3.89 | 44.6 ± 3.43 | 46.0 ± 2.93 | 18.1 ± 0.12 | 4.3 ± 0.92 |

EXAMPLE 10

Each tablet was prepared in accordance with the same procedures as described in Example 7 using 10 mg of bovine somatotropin in place of 10 mg of porcine somatotropin. In vivo test with hypophysectomized rats was carried out in accordance with the procedures as described previously by using the tablet prepared above, and non-treated hypophysectomized rats were used as a control group. The results are shown in Table 6 below. In Table 6, the weight increases are given as mean ± standard deviation.

TABLE 6

| Weight increases in hypophysectomized rats (g) | | |
|---|---|---|
| day | Example 10 | Control |
| 1 | −0.2 ± 1.06 | −1.8 ± 1.07 |
| 2 | 4.9 ± 1.56 | 1.3 ± 1.28 |
| 3 | 5.7 ± 1.25 | −0.6 ± 0.92 |
| 4 | 11.7 ± 0.66 | 0.3 ± 0.76 |
| 5 | 14.5 ± 0.80 | 0.2 ± 0.77 |
| 6 | 17.1 ± 1.00 | 0.5 ± 1.23 |
| 7 | 20.1 ± 1.22 | 0.4 ± 0.71 |
| 8 | 21.7 ± 1.01 | 0.9 ± 1.60 |
| 9 | 23.5 ± 1.34 | 1.3 ± 1.80 |
| 10 | 24.8 ± 1.60 | 0.3 ± 1.89 |
| 11 | 31.2 ± 1.30 | 1.5 ± 1.25 |
| 12 | 32.6 ± 1.24 | 1.5 ± 2.21 |
| 13 | 34.4 ± 1.68 | −0.7 ± 2.33 |
| 14 | 35.8 ± 1.49 | 0.7 ± 2.34 |

TABLE 7

Effects of the present composition on increase of weight and feed efficiency of hogs

| | weight (kg) | | | feed intake (kg) | feed efficiency (improvement %) |
|---|---|---|---|---|---|
| | initial | after 2 weeks (ADG) | after 4 weeks (ADG) | | |
| control | 68.82 | 80.10 (0.81) | 92.05 (0.83) | 85.93 | 3.70 |
| test group | 68.62 | 82.06 (0.96) | 93.30 (0.88) | 79.56 | 3.22 (13.0%) |

As can be seen from the above, the compositions prepared in accordance with the present invention exhibit sustained effect when administered in vivo and can be prepared by a simple process. In addition, they have little side effects, rendering it suitable for long-term administration.

While the invention has been described with respect to the above specific embodiments, it should be recognized that various modifications and changes which may be apparent to those skilled in the art to which the invention pertains may be made and also fall within the scope of the invention as defined by the claims that follow.

What is claimed is:

1. A release-controlled implantable composition consisting of polyethylene glycol in an amount ranging from 30 to 50% by weight and a biocompatible wax in an amount ranging from 30 to 50% by weight based on the total amount of the composition, and somatotropin in an effective amount to exhibit its biological activity in vivo.

2. The composition of claim 1, wherein the somatotropin is an animal somatotropin.

3. The composition of claim 2, wherein the somatotropin is an animal somatotropin.

4. The composition of claim 1, wherein the somatotropin is prepared by a recombinant DNA technology.

5. The composition of claim 1, wherein the somatotropin is a lyophilized somatotropin.

6. The composition of claim 1, wherein the molecular weight of the polyethylene glycol ranges from 1,000 to 40,00 daltons.

7. The composition of claim 1, wherein the biocompatible wax is paraffin wax.

8. The composition of claim 1, wherein the implantable composition is in the form of a tablet or a pellet.

9. The composition of claim 8, wherein the tablet has the size of 3 to 15 mm in diameter and 1 to 10 mm in thickness.

* * * * *